(12) United States Patent
Mistretta et al.

(10) Patent No.: US 7,333,588 B2
(45) Date of Patent: Feb. 19, 2008

(54) VIRTUAL SPHERICAL ANODE COMPUTED TOMOGRAPHY

(75) Inventors: Charles A. Mistretta, Madison, WI (US); Thomas R. Mackie, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 114 days.

(21) Appl. No.: 10/498,383

(22) PCT Filed: Dec. 13, 2002

(86) PCT No.: PCT/US02/39830

§ 371 (c)(1),
(2), (4) Date: Dec. 3, 2004

(87) PCT Pub. No.: WO03/051201

PCT Pub. Date: Jun. 26, 2003

(65) Prior Publication Data

US 2005/0123092 A1  Jun. 9, 2005

Related U.S. Application Data

(60) Provisional application No. 60/341,560, filed on Dec. 14, 2001.

(51) Int. Cl.
*A61B 6/03* (2006.01)
(52) U.S. Cl. .............................. 378/10; 378/4
(58) Field of Classification Search .................. 378/21, 378/22, 27, 62, 119, 136, 137, 143, 4, 10
See application file for complete search history.

(56) References Cited

U.S. PATENT DOCUMENTS

| | | | | |
|---|---|---|---|---|
| 4,042,811 A * | 8/1977 | Brunnett et al. | ............... | 378/14 |
| 4,144,457 A * | 3/1979 | Albert | .......................... | 378/19 |
| 4,144,547 A | 3/1979 | Stoffel | | |
| 4,709,382 A * | 11/1987 | Sones | .......................... | 378/62 |
| 4,718,075 A * | 1/1988 | Horn | .......................... | 378/137 |
| 5,042,487 A * | 8/1991 | Marquardt | .................... | 378/17 |
| 5,383,231 A * | 1/1995 | Yamagishi | .................... | 378/15 |
| 5,469,486 A * | 11/1995 | Hu et al. | ........................ | 378/4 |
| 5,625,661 A * | 4/1997 | Oikawa | ........................ | 378/15 |
| 5,633,906 A | 5/1997 | Hell et al. | | |
| 5,663,995 A * | 9/1997 | Hu | ................................ | 378/15 |
| 5,671,263 A * | 9/1997 | Ching-Ming | ................... | 378/8 |

(Continued)

FOREIGN PATENT DOCUMENTS

DE           4228559 A1 *   3/1994

(Continued)

OTHER PUBLICATIONS

Katsevich, Alexander, Theoretically Exact Filtered BackProjection-Type Inversion Algorithm for Spiral CT, Siam Journal on Applied Mathematics, vol. 62, No. 6.

(Continued)

*Primary Examiner*—Chih-Cheng G Kao
(74) *Attorney, Agent, or Firm*—Boyle Fredrickson S.C.

(57) ABSTRACT

An x-ray computed tomography system uses a broad area x-ray emitter and detector to allow both in plane and out of plane x-ray projections not restrained to spiral or helical scans.

21 Claims, 3 Drawing Sheets

U.S. PATENT DOCUMENTS

| | | | |
|---|---|---|---|
| 5,737,382 A * | 4/1998 | Stierstorfer | 378/19 |
| 5,841,828 A | 11/1998 | Gordon et al. | |
| 5,841,830 A * | 11/1998 | Barni et al. | 378/15 |
| 5,841,831 A | 11/1998 | Hell et al. | |
| 6,075,836 A * | 6/2000 | Ning | 378/17 |
| 6,141,398 A * | 10/2000 | He et al. | 378/4 |
| 6,275,561 B1 * | 8/2001 | Danielsson | 378/15 |
| 6,424,692 B1 * | 7/2002 | Suzuki | 378/4 |
| 6,522,721 B1 * | 2/2003 | Lustberg | 378/143 |

FOREIGN PATENT DOCUMENTS

| | | |
|---|---|---|
| EP | 0 471 455 | 2/1992 |

OTHER PUBLICATIONS

Grangeat, P., An Analysis of the Divergent Beam X-Ray Transform Based on the 3D Radon Transform, Seminar at Mathematicshes Forshunginstitut Oberwolfach: Theory and Application of Radon Transforms, 1986.

Patent Abstracts of Japan, vol. 1998, No. 13, Nov. 30, 1998 & JP 10 211196 A (Olympus Optical Co. Ltd.); Aug. 11, 1998.

International Search Report under date of mailing of Jun. 25, 2003, corresponding to PCT/US02/39830.

* cited by examiner

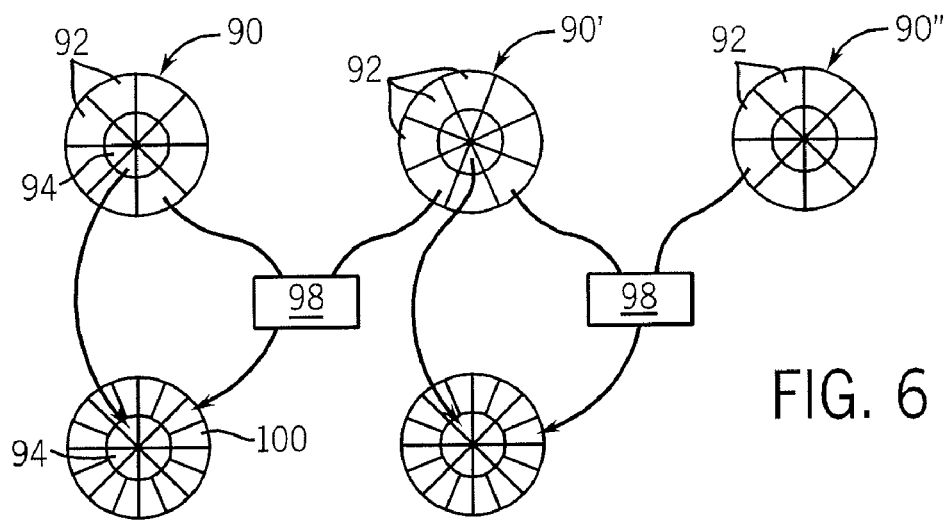
FIG. 6
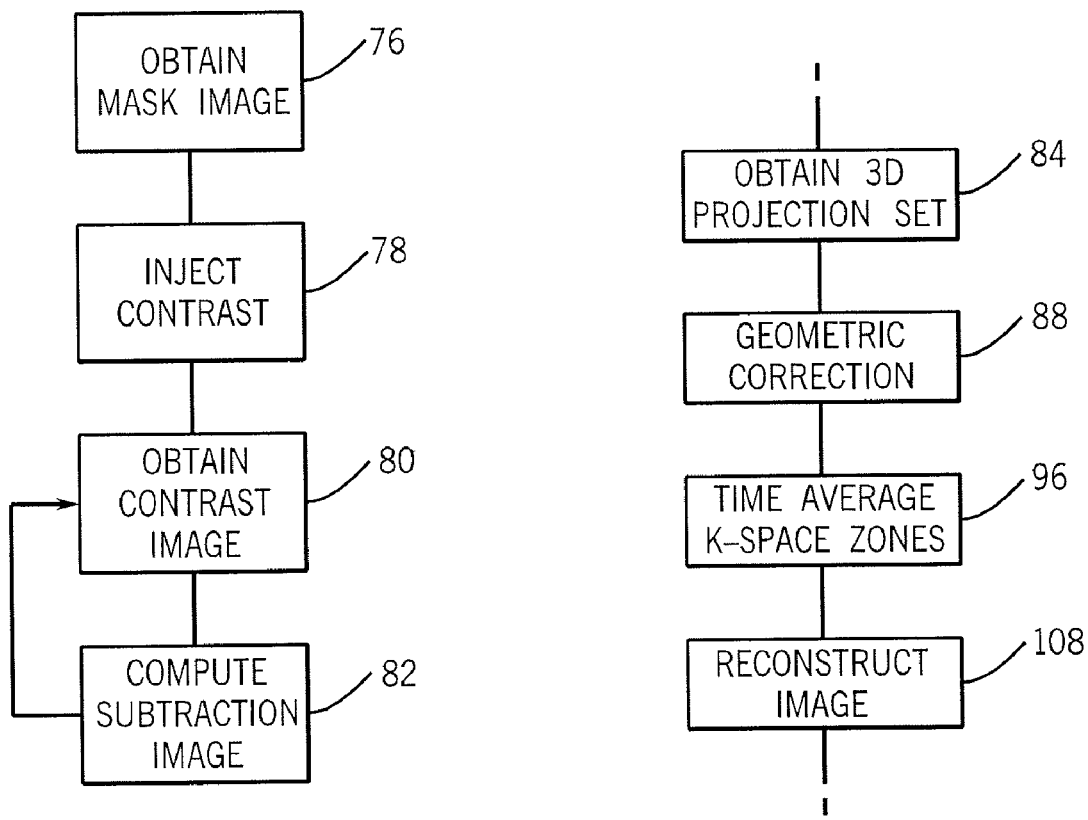
FIG. 7
FIG. 8

VIRTUAL SPHERICAL ANODE COMPUTED TOMOGRAPHY

CROSS-REFERENCE TO RELATED APPLICATIONS

This application is based on provisional application 60/341,560 filed Dec. 14, 2001 and entitled "Virtual Spherical Anode Computer Tomography".

STATEMENT REGARDING FEDERALLY SPONSORED RESEARCH OR DEVELOPMENT

This invention was made with United States government support awarded by the following agencies: NIH HL62425. The United States has certain rights in this invention.

BACKGROUND OF THE INVENTION

The present invention relates to x-ray computed tomography (CT) and specifically to a CT system and method providing high-speed data acquisition.

Conventional x-ray computed tomography may employ an x-ray source collimated to produce a narrow fan-shaped beam directed along the transverse plane through a patient to be received by linear multi-element detector array.

The x-ray source and detector array may be mounted on a gantry to be rotated about a patient to obtain "projections" measuring x-ray attenuation at the different gantry angles along a slice plane though the patient. A "projection set" of such projections, for example, of projections obtained over a range of gantry rotation of 180 degrees plus the angle subtended by the fan beam, may be "reconstructed" into a tomographic image. The tomographic image shows a cross section of the patient along the slice plane.

The collection of a projection set can be viewed as an acquisition of lines of data in "k-space". Each projection (i.e. the x-ray attenuation values measured by each element of the multi-element detector at one gantry angle) provides one line of data in a k-space plane at the same gantry angle and in the slice plane. A projection set provides a series of lines of k-space data extending like spokes of a wheel from the center of k-space. K-space is a frequency domain version of the tomographic image, with data near the center of k-space representing low-frequency image data and data at the edges of k-space providing high-frequency image data. A two-dimensional Fourier transform of k-space data collected by the projections provides the tomographic image.

Reconstructions using too few projections or a limited number of gantry angles may produce images with "artifacts", typically streaks, that mar the tomographic image.

In a normal CT acquisition, multiple projection sets are obtained along different, sequential slice planes by movement of the patient within the gantry. The slices may be assembled to provide data for an arbitrary volume of the patient which may then be reconstructed into cross-sectional images along arbitrary planes.

The time required to collect projection data over a volume using conventional fan-beam tomography can be substantial and may preclude the use of tomography in situations where large volumes are to be monitored in real-time (for example, in contrast studies) or where there is unavoidable patient or organ motion during the acquisition time.

One method of increasing CT acquisition speed is by using a spiral or helical scan in which the gantry containing the x-ray source and detector is rotated continuously as the patient is moved. This process eliminates the need for stopping and starting the gantry and table.

Wider fan beams may also be used with rectangular detector arrays having, for example, 500 or 1,000 detector elements in the scan plane and sixteen detector elements perpendicular to the scan plane. This arrangement allows multiple slices to be collected at one time or allows for a steeper helical pitch.

While these systems provide for more rapid data acquisition, they are fundamentally limited by the rotational speed of the gantry. This latter limitation has been addressed by "electron beam" systems in which a steerable electron beam scans a hemi-cylindrical anode array providing what is in effect an x-ray source rotating about the patient within a plane but without mechanical movement.

SUMMARY OF THE INVENTION

The present invention provides improved volumetric acquisition of CT data by breaking free from the planar acquisition pattern to acquire sequential projections both aligned with and oblique to the slice plane. K-space is filled, not on a plane-by-plane basis, like spokes on wheels but in a three-dimensional starburst pattern. This out-of-plane acquisition provides a number of benefits including the ability to collect missing k-space data caused by beam divergence without patient translation, increased flexibility in selecting projection angle to minimize or measure tissue motion, and the ability to rapidly collect sparse projection sets for large volume imaging on a real time basis without being constrained to a helical or orbital acquisition sequence.

In this regard, the acquisitions of the present invention are analogous to three-dimensional isotropic magnetic resonance imaging (MRI) in which the x, y and z magnetic gradient fields are rapidly switched to allow for "projection" angles sampling three dimensions of k-space in a short time. When used with magnetic resonance imaging, this multi-dimensional sampling allows for time-resolved angiography and other dynamic applications in which it is desired to follow the time course of an image contrast medium.

Unlike magnetic resonance imaging, however, in which different projection angles may be obtained simply by changing the gradient fields, in x-ray CT, an actual x-ray beam at different three-dimensional angles must be obtained. The present invention addresses this problem with a large-area x-ray emitter that approximates a spherical source. A broad-area detector opposing the anode allows full utilization of the data obtained both in and out of slice plane. Undersampling and interleaving can be used to further decrease sampling time.

Specifically, the present invention provides an x-ray tomography system having a patient support and an x-ray source positionable proximate to the patient support. The x-ray source may include an areal anode and an electron gun where the electron gun is on the opposite side of the areal anode with respect to the patient support and is steerable to direct a beam of electrons at a rear side of the areal anode to cause the transmissive emission of x-rays from a front side of the areal anode. The x-rays are directed toward at least one point on the patient support over a range of latitudinal and longitudinal angles, at least one of which is no less than 180 degrees.

A multi-element detector opposes the x-ray source about the patient support for receiving the x-rays and a controller communicates with the x-ray source and the multi-element detector to steer the electron beam to acquire a series of projection sets each including measurements of x-ray attenuation of x-rays over the range of latitudinal and longitudinal angles.

Thus, it is one object of the invention to provide an x-ray CT machine that may acquire freely acquire projections outside of a single-slice plane.

The areal anode may be curved about the patient support.

It is another object of the invention to provide increased angular projection range for a given anode area.

The areal anode may be a hemi-cylinder.

Thus, it is an object of the invention to provide a compact anode shape that accommodates a patient, for example, supine on a patient table.

The tomography system may contain a geometric corrector receiving the projections and weighting them to simulate projection sets acquired with a hemispherical anode.

Thus, it is another object of the invention to provide for the use of a convenient hemi-cylindrical or other non-spherical anode surfaces while minimizing artifacts caused by varying source-to-patient distances.

The areal anode may be a portion of a sphere.

Thus, it is an object of the invention to provide a simple surface that requires no geometric correction.

The detector may be planar, curved about the patient in a hemi-cylinder or a section of a sphere.

Thus, it is another object of the invention to provide flexibility to use standard planar detector arrays, or alternatively, to use detector arrays that have minimized surface areas.

The detector and areal anode may be curved about the patient support and the detector may be x-ray transmissive and include a portion fitting between opposed surfaces of the areal anode.

Thus, it is another object of the invention to provide a method of obtaining greater than 180 degrees of x-ray beam angle necessary for artifact free tomographic reconstruction without mechanical movement.

The areal anode may include a collimator.

Thus, it is another object of the invention to provide for scatter reduction with a fixed areal anode.

The areal anode's surface may be dimpled to intercept the electron beam.

Thus, it is yet another object of the invention to allow optimization of the anode surface for multiple x-ray angles.

These particular objects and advantages may apply to only some embodiments falling within the claims and thus do not define the scope of the invention.

BRIEF DESCRIPTION OF THE DRAWINGS

FIG. 6 is a diagrammatic representation of successive k-space acquisitions using a averaging process used to offset the sparsity of high-frequency data;

FIG. 7 is a flow chart of use of the invention during acquisition of a contrast image;

FIG. 8 is a flow chart showing the steps of obtaining each of the images of FIG. 7;

DETAILED DESCRIPTION OF THE PREFERRED EMBODIMENT

Figure 1:
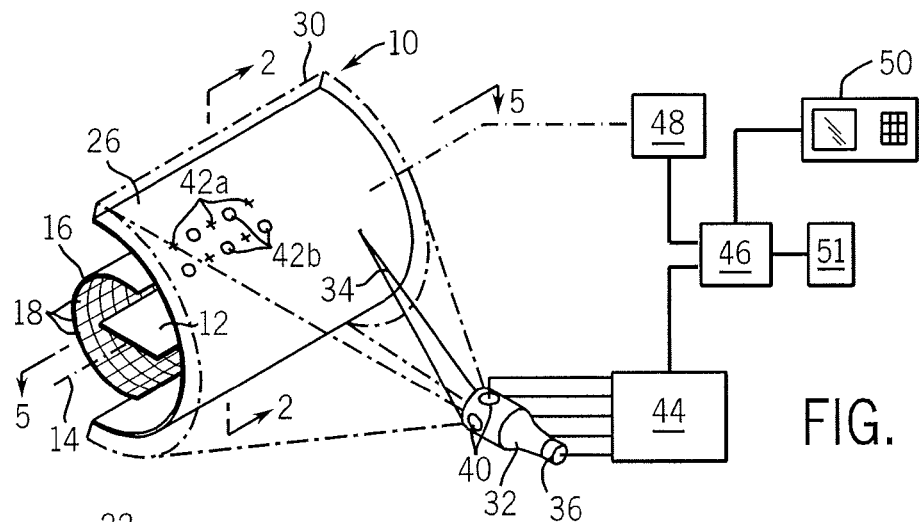
FIG. 1 is a simplified perspective view of a CT machine suitable for acquiring out-of-plane projections per the present invention and having co-axial opposed hemi-cylindrical anodes and detectors about a patient table.

Referring to FIG. 1, a CT system 10 suitable for use with the present invention provides a horizontal patient table 12 extending generally along a longitudinal axis 14 on which a patient (not shown) may be supported in a supine position.

A detector array 16 is curved about the patient table 12 following the curved wall of a hemi-cylinder whose axis is aligned with the longitudinal axis 14. The inner surface of the detector array 16 supports a series of detector elements 18 arranged in rows and columns facing the patient table 12. The detector elements 18 may thus receive x-rays transmitted through the patient on the patient table 12 from a variety of different latitudinal angles 22 being generally those in a vertical plane or longitudinal angles 24 being generally those in a horizontal plane. The detector elements 18 may be conventional scintillation type x-ray detectors but may also include ionization type or CZT detectors or other such detectors well-known in the art and preferably attain at least a thirty frame-per-second readout speed.

Opposite to the detector array 16, with respect to the table 12, is an areal anode 26 also curved around the patient table 12 to follow the curved wall of a hemi-cylinder aligned along the longitudinal axis 14. The diameter of curvature of the areal anode 26 is greater than that of the detector array 16 so that it may partially enclose the latter. The areal anode 26 can be constructed, for example, of an outer supporting material of low-Z such as beryllium, and an inner target material of high-Z material such as tungsten. The target material faces the patient table 12.

Areal anode 26 is held within an airtight housing 30 that is evacuated and also encloses an electron gun 32. Electron gun 32 is displaced horizontally so that the areal anode 26 is between the patient table 12 and the electron gun 32. An electron beam 34 from the electron gun 32 may pass through the beryllium of the areal anode 26 to strike the tungsten to produce an x-ray beam directed toward the patient table 12.

The electron gun 32 includes an electron source 36, for example a heated filament, to produce electrons that are formed into an electron beam 34 drawn toward the areal anode 26 by an accelerating voltage maintained between the areal anode and electron gun 32. Electrostatic or magnetic yokes 40 positioned about the electron gun 32 allow steering of the electron beam 34 to a variety of arbitrary target spots 42a and 42b.

The yokes and electron source 36 may communicate with a gun control circuit 44 connected via a bus to a computer 46 that may thus control the electron beam 34 turning it on and off and selecting the particular focal spot 42a or 42b to which the electron beam 34 is directed. Ideally, thirty or more different focal spots 42 per second would be targeted. Various focus change coils (not shown) may also be controlled by computer 46 to accommodate the difference in distance between the electron gun 32 and the areal anode 26 for the different focal spots 42a and 42b.

Computer 46 also communicates with table control 48 that provides for translation of the table 12 along the longitudinal axis 14 during scanning as will be described. An operator console 50 provides for input of data to the computer 46 for control of the CT system 10 and for the readout of the images and other data which may be stored on mass storage device 51 also communicating with computer 46.

Figure 2:
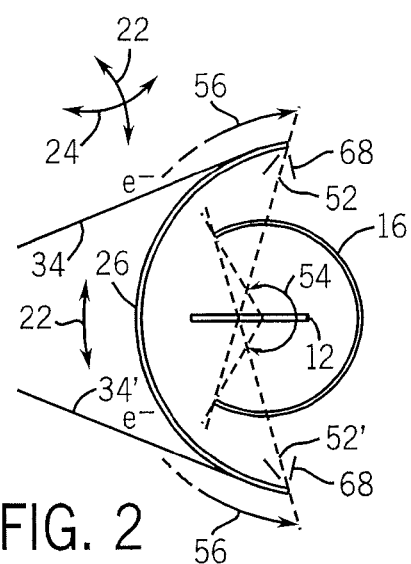
FIG. 2 is a cross-sectional view along line 2-2 of FIG. 1 showing overlap of the detector and anode such as allows for greater than 180 degrees range of projection angle within a slice-plane.

Referring now to FIG. 2, the detector array 16 may subtend an latitudinal angle 22 of substantially greater than 180 degrees about a patient on the patient table 12, and ideally, will extend in an angular range 54 somewhat more than 180 degrees so as to be able to receive data for a complete projection set within a slice plane perpendicular to the longitudinal axis 14. The areal anode 26 will extend in a range of latitudinal angles 22 of less than 180 degrees dictated by the requirement that the electron beam 34 from a single electron gun 32 to be able to strike its outer surface. This requirement may be relaxed if multiple vertically displaced electron guns are used. Nevertheless, the larger diameter of the areal anode 26, with respect to the diameter of the detector array 16, is selected so that the areal anode 26 may partially surround the detector array 16. In this way, electron beams 34 and 34' representing the highest and lowest limits of a range of latitudinal angles 22 obtainable by the electron gun 32, when striking the areal anode 26 can produce cone beams of x-rays having central rays 52 and 52' that flank a range 56 of latitudinal angles 22 of over 180 degrees.

Figure 5:
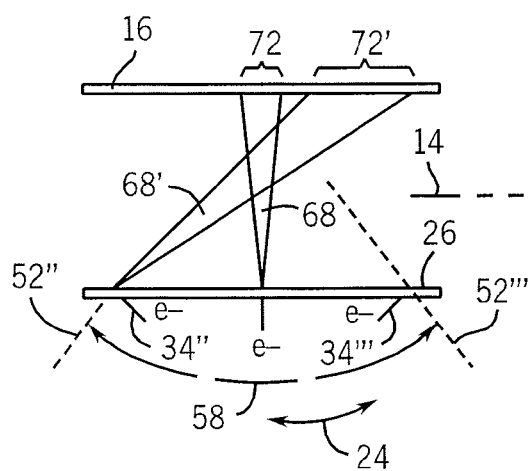
FIG. 5 is a cross-sectional view along 5-5 of FIG. 1 showing a geometric error introduced using a hemi-cylindrical rather than a hemispherical detector and anode.

Referring to FIG. 5, a lesser range 58 of longitudinal angles 24 of central rays 52" and 52'" may be obtained using electron beams 34" and 34'" at the limits of the longitudinal angles 24 of the electron gun 32. Typically, this angle will be at least twenty-five degrees to ninety degrees. This angular range is sufficient to fill in the k-space data normally lost by divergence of a cone beam scanned about a single slice plane. Greater angles are limited by excessive path length through the supine patient.

The angular ranges 54, 56, and 58 may be measured along a surface of an imaginary sphere located so that the surface of the sphere at points of intersection between the center rays and the spherical surface is normal to the central rays 52.

Figure 3:
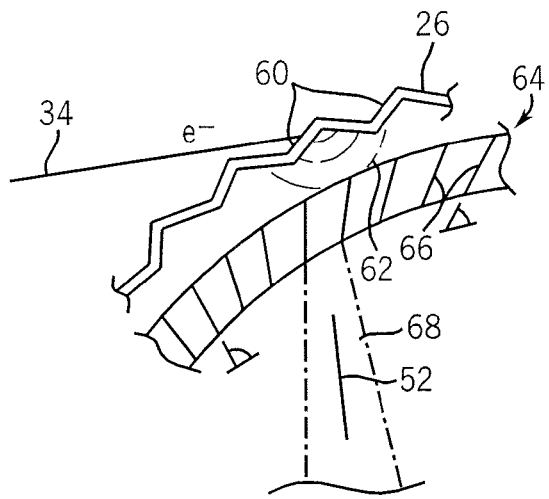
FIG. 3 is a detailed fragmentary view of the anode of FIG. 2 showing a dimpling of its surface to provide for an improved electron target and showing an associated collimator.

Referring now to FIG. 3, the areal anode 26 may include a stepped or dimpled surface providing a series of targets 60 that the electron beam 34 may strike. X-rays 62 emitted from the inside of the areal anode 26 may be received by a collimator 64 having laminae 66 forming x-ray 62 into a cone-beam 68 of the desired size, desired central ray 52, and causing reduced scatter. The laminae 66 may change in angle over the surface of the areal anode 26.

Figure 4:
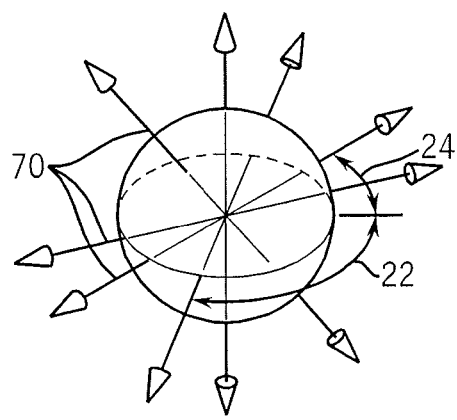
FIG. 4 is a diagram of k-space showing normals to acquisition planes in k-space obtained with the present invention.

Referring now to FIG. 4, the area of detection provided by the detector array 16 allows a series of different projection planes in k-space to be obtained with normals 70 having arbitrary latitudinal angles 22 and longitudinal angles 24. Using cone beams 68 prevents direct acquisition of k-space data because of partial volumes covered by the diverging beams. K-space data can however be created from images reconstructed using cone beam algorithms such as those taught by Greaneat or Katsevich. See generally, P. Grangeat, Theoretical background of the cone beam reconstruction algorithm. Doctoral thesis, Ecole Nationale Supericure des Telecommunications, 1987; P. Grangeat, An analysis of the divergent beam X-ray transform based on the 3D Radon transform. Presented at the seminar at the Mathematicshes Forshunginstitut Oberwolfach: Theory and Applications of Radon Transforms., 1986; A. Katsevitch, Theoretically exact FBP-type inversion algorithm for spiral CT, SIAM Journal on Applied Mathematics 62(2002), 2012-2026, hereby incorporated by reference.

These normals 70 are generally aligned with the central rays 52 of the x-ray beams 68. Per the central slice theorem, a set of evenly distributed planes within a spherical k-space volume may be obtained. To the extent necessary, the data of the detector elements 18 may be interpolated and rebinned to provide the proper orientation of the planes. Alternatively, this adjustment may be performed by interpolation (for example to a grid) in k-space.

Referring to FIG. 5, the hemi-cylindrical shape of the detector array 16 and an areal anode 26 will cause a geometric intensity variation among projections. For example, the first x-ray beam 68 extending approximately perpendicularly to the longitudinal axis 14 will have a smaller detector footprint 72 than a detector footprint 72' of a similarly diverging beam 68' canted with respect to the longitudinal axis 14. This geometric distortion may be corrected by a set of weighting factors determined mathematically or empirically for the particular geometry of the detector array 16 and the areal anode 26. The weighting factors are applied to the measured projections so as to produce a set of attenuation measurements at the detector array 16 that are equivalent to a detector array 16 and areal anode 26 that spherical in shape. Other standard CT processing of the data may also be performed.

Referring now to FIG. 7, the present invention is particularly well-adapted to following contrast agents injected into the body of the patient where the flexibility of positioning the projections permits a more uniform, sparse collection of k-space data. In such a study, as indicated by initial process block 76, a mask image is first obtained of the volume of interest. This mask image may typically be acquired at a high resolution and obtained by directing the electron gun 32 to a large number of target areas 42a and 42b on the surface of the areal anode 26.

At process block 78, x-ray contrast media is injected into the patient and at process block 80 a series of contrast image acquisitions is begun.

Referring to FIG. 8, for each contrast image, a sparse projection set may be acquired per process block 84. At process block 88, geometric and other necessary CT corrections are performed on these projections and k-space data 90, shown in FIG. 6, can be developed from the projections as described above. This k-space data set 90 desirably includes projections whose center rays are distributed in both latitudinal angle 22 and longitudinal angle 24 but provides sparse k-space data in an outer region 92 and more highly sampled k-space data in an inner region 94 as a result of a radial convergence/divergence of the planes of data. This outer region 92 corresponds to high-frequency image data and the inner region 94 responds to low-frequency image data.

The sparsity of high-frequency image data of the outer region 92 allows rapid acquisition of volume data but will generally produce image artifacts. Accordingly, at a process block 96, following the geometric correction, an averaging of k-space data is performed wherein a second subsequent k-space data set 90' is acquired and the data of the outer region 92 of k-space data set 90' is averaged through averaging block 98 to produce an averaged outer region 100. This second k-space data set 90 preferably uses different projections (e.g. by using focal spots 42b when k-space data set 90 using focal spots 42a). The inner region 94 of k-space data set 90 is then spliced directly into the inner region 94 of the k-space data set 90' and the combined k-space inner region 94 and averaged outer region 100 is reconstructed by a three dimensional Fourier transform as indicated by process block 108 of FIG. 8. In this way, data artifacts are significantly reduced while providing essentially real-time imaging of low-frequency data.

It will be understood that these zones in k-space need not be distinct zones, but may involve a continuous weighting function, and further, that the averaging may be conducted with a weighting function over two or more successive k-space datasets 90, 90' and 90" and may also be conducted for the data of the inner region 94 using a different averaging window than that used for the outer region 92. Variations of temporal filtering could include the use of matched filtering to weight sequential time frames in response the degree of contrast present at each point in time.

At process block 82, the mask image and the contrast image (as averaged) may be subtracted to provide an image providing substantially showing the contrast media alone. The steps of process blocks 80 and 82 may be repeated so as to provide a real-time indication of the motion of the contrast medium through the body. During the acquisition of either of the mask and contrast images, motion of the table 12 may be provided, if necessary to provide for additional projection angles or to reduce the longitudinal length of the detector array 16 and areal anode 26 or to increase the possible imaging volume that may be obtained.

The above image processing steps, including reconstruction of an image from k-space data, may be performed by the computer 46 executing a stored program employing the above steps augmented by steps well known in the art.

Figure 9:
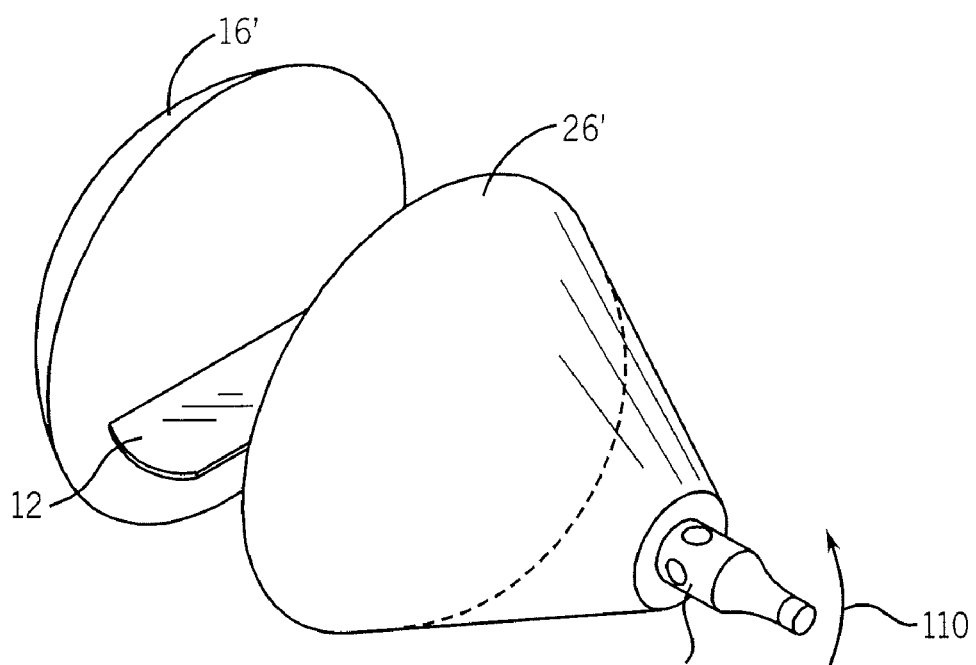
FIG. 9 is a view similar to that of FIG. 1 showing an alternative embodiment of the of FIG. 1 having hemispherical detector and anode.

Referring now to FIG. 9, geometric correction may be eliminated by using a truly hemispherical detector array 16' and hemispherical areal anode 26'. Such a detector array 16' and anode 26' may be overlapped as shown in FIG. 2 to provide proper projection set ranges, or alternatively, the detector array 16' and anode 26' may be rocked slightly about the patient by a motion 110. This latter approach which may also allow separating between the detector array 16' and the areal anode 26' as shown for improved patient access.

Figure 10:
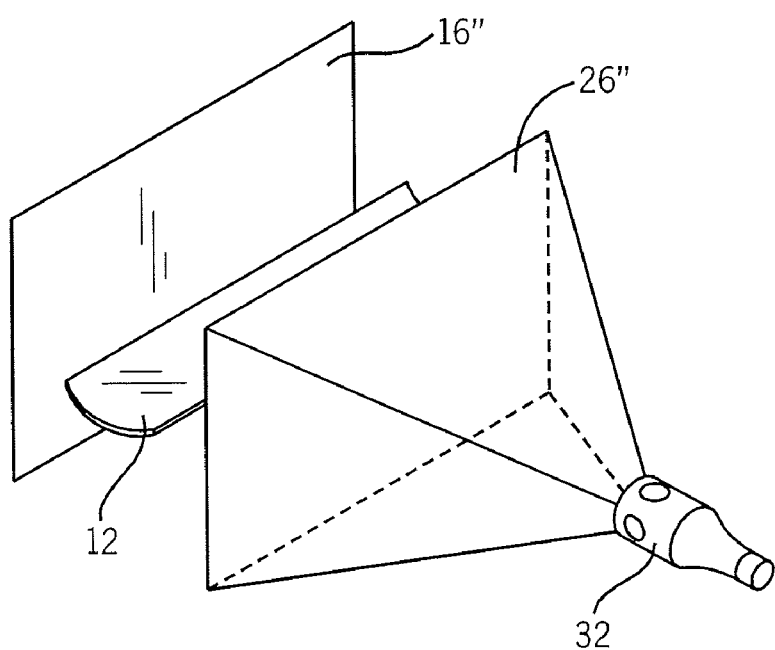
FIG. 10 is a figure similar to that of FIGS. 1 and 9 showing CT machine having a planar anode and detector array.

A similar system may use planar detector array 16" and planar areal anode 26" such as simplifies fabrication, but requires a larger area for comparable longitudinal range as shown in FIG. 10.

It is specifically intended that the present invention not be limited to the embodiments, and illustrations contained herein, but include modified forms of those embodiments including portions of the embodiments and combinations of elements of different embodiments as come within the scope of the following claims. For example, the areal anode system described may be replaced by multiple distributed x-ray sources performing a similar function, for example, to those using multiple electron guns. The invention may be used with a stationary table, a periodically incremented table or with constant table motion. An alternative to the angiographic application described above is the imaging of anatomical regions such as the lung for the purpose of tumor detection. In this case, bone subtraction using the thresholding and reprojection method may be used.

We claim:

1. An x-ray tomography system comprising:
   a patient support;
   an x-ray source positionable proximate to the patient support and including:
   i) an areal anode; and
   ii) an electron gun on an opposite side of the areal anode with respect to the patient support, the gun steerable to direct a beam of electrons at different portions of a rear side of the areal anode to cause transmissive emission of x-rays from a front side of the areal anode at different latitudinal and longitudinal angles, the x-rays directed toward at least one point on the patient support over a range of latitudinal angles and a range of longitudinal angles, at least one of which ranges is no less than 180 degrees;
   a multi-element detector opposed to the x-ray source about the patient support; and
   a controller communicating with the x-ray source and the multi-element detector to steer the electron beam to acquire multiple angles of measurements of x-ray attenuation through the point on the patient support at each position of the x-ray source;
   wherein the areal anode is curved about the patient support.

2. The x-ray tomography system of claim 1 wherein the areal anode is a hemicylinder.

3. The x-ray tomography system of claim 2 including a geometric corrector receiving projection sets and weighting them to simulate projection sets acquired with a hemispherical areal anode.

4. The x-ray tomography system of claim 1 wherein the areal anode is a portion of a sphere.

5. The x-ray tomography system of claim 1 wherein the detector is a hemicylinder and the detector is curved about patient.

6. The x-ray tomography system of claim 1 including a geometric corrector receiving projection sets and weighting them to simulate projection sets acquired with a hemispherical detector.

7. The x-ray tomography system of claim 1 wherein the detector is a surface defining a sphere.

8. The x-ray tomography system of claim 1 wherein the detector is curved about the patient support and wherein the detector is x-ray transmissive and includes a portion fitting between opposed surfaces of the areal anode.

9. The x-ray tomography system of claim 1 wherein the areal anode includes a collimator.

10. The x-ray tomography system of claim 1 wherein an areal anode surface is dimpled in a predetermined pattern to define a series of target areas for intercepting oblique electron beams on one side and transmitting x-rays at predetermined angles from an obverse side.

11. An x-ray tomography system comprising:
    a patient support;
    an x-ray source positionable proximate to the patient support and providing an x-ray emitting surface selectively directing x-rays toward the patient support over a range of latitudinal and longitudinal angles about points within a patient on the patient support of at least twenty-five degrees for a given position of the x-ray source; and
    a multi-element detector opposed to the x-ray source about the patient support; and a controller communicating with the x-ray source and the multi-element detector to acquire a series of projection sets each including measurements of x-ray attenuation of x-rays over the range of latitudinal angles and longitudinal angles;

wherein the emitting surface is a hemicylinder and the x-ray emitting surface is curved about the patient support.

12. The x-ray tomography system of claim 11 including a geometric corrector receiving the projection sets and weighting them to simulate projection sets acquired with a hemispherical emitting surface.

13. The x-ray tomography system of claim 11 wherein the detector is a hemicylinder and the detector is curved about the patient support.

14. The x-ray tomography system of claim 11 including a geometric corrector receiving the projection sets and weighting them to simulate projection sets acquired with a hemispherical detector.

15. The x-ray tomography system of claim 11 wherein the detector is a surface defining a sphere.

16. The x-ray tomography system of claim 11 wherein the emitting surface includes a collimator.

17. An x-ray tomography system comprising:

a patient support;

an x-ray source positionable proximate to the patient support and providing an x-ray emitter selectively directing x-rays toward at least one point within a patient supported by the patient support over a range of latitudinal and longitudinal angles;

wherein the x-ray source provides an areal anode and an electron gun on an opposite side of the areal anode with respect to the patient support, the gun steerable to direct a beam of electrons at a rear side of the areal anode to cause transmissive emission of x-rays from a front side of the areal anode, the x-rays directed toward at least one point in the patient over a range of latitudinal angles and a range of longitudinal angles, at least one of which ranges is no less than 180 degrees, wherein a shape of the areal anode is selected from a group consisting of a portion of a cylinder and a portion of a sphere;

a multi-element detector opposed to the x-ray source about the patient support;

a controller communicating with the x-ray source and the multi-element detector to acquire a series of projection sets each including measurements of x-ray attenuation of x-rays over the range of latitudinal angles and longitudinal angles; and a reconstructor receiving the projection sets to produce a series of tomographic images in which each image includes data combined from different projection sets so that high frequency image data of the projection sets is combined from more projection sets than lower frequency image data.

18. The x-ray tomography system of claim 17 wherein the controller uses x-rays with different latitudinal and longitudinal angles to acquire different sequential projection sets.

19. A method for producing computed tomographic images comprising the steps of:

a) exposing a patient to a series of x-ray cone beams along axes normal to and distributed with respect to the patient over an areal portion of a surface defining a spherical anode;

b) detecting the beams after passage through the patient with a multi-element detector subtending a solid angle of at least twenty-five degrees; and c) reconstructing a tomographic image from the detected beams;

wherein the patient is supported on a table and the table is moved continuously during steps (a) and (b).

20. The method of claim 19 including the step of: (d) repeating steps (a)-(c) wherein the patient is exposed to a series of x-ray cone beams along axes with a different distribution over the portion of a surface.

21. The method of claim 19 in which contrast is injected into the patient before step (a).

\* \* \* \* \*